(12) United States Patent
Gao et al.

(10) Patent No.: US 9,353,380 B2
(45) Date of Patent: May 31, 2016

(54) BRTCP24 GENE USEFUL FOR CONTROLLING GROWTH OF CABBAGE AND APPLICATION THEREOF

(71) Applicant: VEGETABLE RESEARCH INSTITUTE OF SHANDONG, ACADEMY OF AGRICULTURAL SCIENCES, Jinan (CN)

(72) Inventors: Jianwei Gao, Jinan (CN); Fengde Wang, Jinan (CN); Yihui Zhang, Jinan (CN); Lifeng Liu, Jinan (CN); Huayin Li, Jinan (CN); Libin Li, Jinan (CN); Lihua Wang, Jinan (CN); Cuihua Wang, Jinan (CN)

(73) Assignee: VEGETABLE RESEARCH INSTITUTE OF SHANDONG, ACADEMY OF AGRICULTURAL SCIENCES, Jinan (CN)

( * ) Notice: Subject to any disclaimer, the term of this patent is extended or adjusted under 35 U.S.C. 154(b) by 40 days.

(21) Appl. No.: 14/373,145

(22) PCT Filed: Aug. 19, 2013

(86) PCT No.: PCT/CN2013/081752
§ 371 (c)(1),
(2) Date: Jul. 18, 2014

(87) PCT Pub. No.: WO2014/029309
PCT Pub. Date: Feb. 27, 2014

(65) Prior Publication Data
US 2014/0364589 A1    Dec. 11, 2014

(30) Foreign Application Priority Data

Aug. 22, 2012 (CN) .......................... 2012 1 0300995

(51) Int. Cl.
*C07K 14/415* (2006.01)
*C12N 15/82* (2006.01)

(52) U.S. Cl.
CPC .......... *C12N 15/8261* (2013.01); *C07K 14/415* (2013.01)

(58) Field of Classification Search
CPC ......................... C07K 14/415; C12N 15/8261
See application file for complete search history.

(56) References Cited

PUBLICATIONS

Wang et al. 2011; The genome of the mesopolyploid crop species *Brassica rapa*. Nature Genetics. 43(10):1035-1040.*
Wang et al. Sequence Alignment Only for 2011; The genome of the mesopolyploid crop species *Brassica rapa*. Nature Genetics. 43(10):1035-1040.*

* cited by examiner

*Primary Examiner* — Karen Cochrane Carlson
(74) *Attorney, Agent, or Firm* — CBM Patent Consulting, LLC

(57) ABSTRACT

A BrTCP24 gene for controlling the growth of Chinese cabbage and its applications. The BrTCP24 gene has the nucleotide sequence shown in SEQ ID No. 1, the whole length of which is 1221 bp. The gene is useful for improving the production of economic crop. As indicated by experimental results, the gene serves as a controlling gene for plant growth and has the function of down-regulating the plant growth. Through overexpressing the gene, a transgenic plant smaller than the wild one can be obtained. The gene of the invention can provide theory basis and gene source for breeding new varieties of crops.

3 Claims, 1 Drawing Sheet ly controlled by the growth and development of the leaves. Researches on BrTCP24 gene will be helpful to analyze the mechanism of the leaves growth and the leaf head formation of Chinese cabbage, and is of important theoretical significance in controlling the leaf head size of Chinese cabbage genetically and improving the yields and quality of Chinese cabbage.

BRTCP24 GENE USEFUL FOR CONTROLLING GROWTH OF CABBAGE AND APPLICATION THEREOF

This application is the U.S. national phase of International Application No. PCT/CN2013/081752 filed on 19 Aug. 2013 which designated the U.S. and claims priority to Chinese Application Nos. 201210300995.4 filed on 22 Aug. 2012, the entire contents of each of which are hereby incorporated by reference.

TECHNICAL FIELD

The invention relates to a BrTCP24 gene for controlling the growth of Chinese cabbage and its applications, especially a BrTCP24 gene for down regulating the growth of Chinese cabbage and its applications, which belongs to the field of molecular biology technology.

BACKGROUND

The Chinese cabbage (*Brassica rapa* L. ssp. *Pekinensis*) originates in China, which is one of the most important vegetable crops in China and even the world. The leaf head is the main organ of Chinese cabbage for eating, and its size is an important economic property which should be considered in the work of Chinese cabbage breeding at present. It has been demonstrated by many years of production practice that the leaf head size of Chinese cabbage is controlled strictly by genetic and affected by the related gene expression and regulation. It is of important theoretical significance and practical value in controlling leaf head size genetically and improving the yields and quality of crops to start researches on the genes related to the leaf head size of Chinese cabbage.

Although the sizes of plant organs vary considerably between different species, the organs of the individuals within one species possess the relatively uniform size, indicating that the sizes of plant organs are controlled strictly by genetic. Studies have shown that there are multiple genes existing in plant for controlling the sizes of the organs, such as ANT, AtGRF1-AtGRF5, ARGOS, BrARGOS, AtGIF1, STN1, AtMRB1, ANGUSTIFOLIA, AtEXP10, ARL, ROT3, RON2/LUG and BPE genes. They decide the sizes of the organs by regulating cell division and growth. For example, overexpression of AtGRF1 and AtGRF2 in *Arabidopsis thaliana* led to larger leaves and cotyledons. In contrast, the atgrf1-atgrf2-atgrf3 tri-mutant led to smaller leaves and cotyledons. The phenotypic variations were due to the increase or decrease of the cell volume, indicating that the AtGRF protein regulated the cell extension of the leaves and cotyledons tissues. Because of the decreasing number of cells in the width direction of the leaves, the GIF1 function defect mutant led to narrow leaves and petals, indicating that GIF1 gene controlled the growth and shapes of the leaves and petals.

The AINTEGUMENTA (ANT) function defect mutant in *Arabidopsis thaliana* reduced the size and number of the leaves and flowers, while the ectopic expression of ANT gene led to larger vegetative organs (such as leaves and stems) and flower organs. ANT gene altered the sizes of mature organs mainly by affecting the total number and the division extent of the cells. The gene did not control cell growth rate and cell cycle, but regulated the organ growth and cell division during organogenesis. These results indicated that ANT gene probably maintained the sustained cell division which was in coordination with growth. The ANT function defect mutant led to reduction of cell mitosis, early termination of cell growth, and accordingly reduction of the organ size. In contrast, the plants with overexpression of ANT gene could make their own cells grow and divide longer than normal cells, and accordingly possess larger organs. The function of ANT gene is not limited to *Arabidopsis thaliana*, the expression of 35S::ANT also makes the transgene tobacco plants enlarge. ANT gene encodes a transcription factor with an AP2-domain, and its homologues genes have been isolated from other plants. The ectopic expression of rape BANT gene also made the organs of *Arabidopsis thaliana* enlarge, further indicating that ANT genes from different plants possessed conservative function in controlling the organ size.

ARGOS gene functions upstream of the ANT gene and affects the division ability of the organ cells. The plant organs with positive or negative expression of ARGOS gene would be larger or smaller separately, because the changes of the cell number and organ growth duration led to the alteration of organ sizes. Overexpression of ARGOS-LIKE gene in *Arabidopsis thaliana* would make plant organs enlarge. The reason was not the increase of the cell number, but the enlargement of the cell size, indicating that the functions of the homologous genes in controlling the organ size were different.

The TCP family of transcription factors is unique in plant. TCP domain gene plays a key role in developmental regulation, and the different members in different species participate in different morphological development processes. In the TCP family, the first member isolated and identified was the *Cycloidea* (Cyc) gene in snapdragon. Cyc and another TCP family member *Dichotoma* (Dich) together control the asymmetric development of snapdragon flower. When Cyc and Dich were double mutated, the bilateral symmetrical flower of snapdragon would change to radial symmetrical flower. In corn, the TCP family member *Teosinte Branched* 1 (Tb1) controls the tillering capacity of corn. The mutation of Tb1 gene led that the apical dominance of the normal wild corn lost and the lateral buds grew and developed uninhibitedly and sequentially developed to be lateral branches, whose phenotype was very similar to teosinte which is the ancestor of corn. Moreover, PCF 1 and PCF 2, the Cyc/Tb1 homologous gene in rice, also have been cloned. Gene sequence alignment shows that there is a highly conserved domain in the sequences of Tb1, Cyc, PCF1 and PGF2, which can form an untypical Helix-Loop-Helix structure and is composed of about 60 residues. This conserved sequence is named TCP domain which is from the first letter of Tb1, Cyc and PCF. Genes who possess the conserves domain are called TCP domain gene. Based on the characteristic of the TCP domain sequence, the TCP gene family is divided by two subgroups: one is represented by PCF, the other is represented by Cyc and Tb1. They show some differences in biological functions. For example, TCP20 gene that belongs to subgroup I can up-regulate the cell growth, while the CIN, TCP2 and TCP4 genes that belong to subgroup II function oppositely and down-regulate the cell growth.

Therefore, if we find and make use of the genes that control the cell growth of Chinese cabbage and substantially control the organ size, it will play a very important role in the improvement of the quality of Chinese cabbage.

SUMMARY OF THE INVENTION

For overcoming the shortage in the art, a BrTCP24 gene for controlling the growth of Chinese cabbage and its applications are provided in the invention.

A BrTCP24 gene for controlling the growth of Chinese cabbage, wherein the nucleotide sequence is shown as SEQ ID No. 1.

The BrTCP24 gene mentioned above has the whole length of 1221 bp, encoding 406 amino acids. The AtTCP4 gene of *Arabidopsis thaliana* has a close relationship with BrTCP24 gene in the evolution, wherein the identity of their nucleotide sequences is only 77.15% and the identity of amino acid sequences is only 77.57%, indicating the great difference between these species.

A polypeptide encoded by the BrTCP24 gene mentioned above, wherein the amino acid sequence is shown as SEQ ID No. 2.

A recombination vector inserted by the nucleotide sequence shown as SEQ ID No. 1.

The applications of the BrTCP24 gene and the recombination vector mentioned above in improving the production of economic crop.

Advantages

In the invention, the BrTCP24 gene was cloned from Chinese cabbage and was proved to possess the function of downregulating the growth of plant cells. Experiments have shown that overexpression of the gene led to a transgene plant which was smaller than the wild plant. The gene of the invention can provide theory basis and gene source for breeding new varieties of crops.

FIGURE DESCRIPTION

EMBODIMENT

Figure 1:
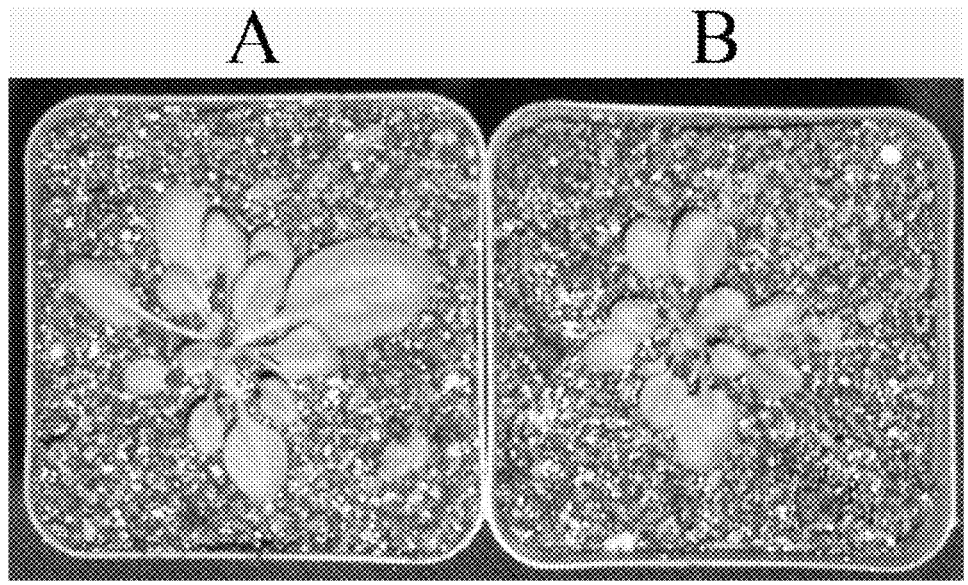
FIG. 1 is the contrast pictures of the wild and transgene *Arabidopsis thaliana* plants growing on vermiculite for 30 days. A is the wild type plant, and B is the transgene plant overexpressing the BrTCP24 gene.

The following is the detail description of the present invention with examples and appended drawings. The scope of the present invention is not limited thereof.

EXAMPLES

Extracting of mRNA from Chinese Cabbage

Take the overground part of the 10 days old seedling of the Fushan Baotou variety of Chinese cabbage as the material, put in a mortar pre-cooling by the liquid nitrogen, add liquid nitrogen and power fast, load 100 mg power into 1.5 ml centrifuge tube, add 1 ml Trizol (purchased from Invitrogen Corporation) and mix by inverting, settle for 10 min at room temperature. Centrifuge at 4° C., 12000 rpm for 10 min, transfer the supernatant to a new 1.5 ml centrifuge tube. Add 200 ul chloroform, shake vigorously for 15 sec by hand, settle for 2-3 min at room temperature. Centrifuge at 4° C., 12000 rpm for 10 min, transfer the upper aqueous phase colorless to a new 1.5 ml centrifuge tube, add 600 µl isopropanol pre-cooling in −20° C. refrigerator, mix by inverting, settle for 10 min at room temperature. Centrifuge at 4° C., 12000 rpm for 10 min, discard the supernatant. Add 1 ml 75% (v/v) ethanol and vortex. Centrifuge at 4° C., 7500 rpm for 3 min. Dry for 3-5 min at room temperature, add 30 ul $H_2O$ without RNase to resolve the sediment, resolve for 10 min at 55° C. water bath, cool fast for 5 min by ice bath and centrifuge transiently to obtain mRNA.

Obtaining of the BrTCP24 Gene

Amplify the BrTCP24 gene coding sequence by the RT-PCR method. The detailed operating method was as follows:

Reverse transcribe the obtained mRNA to the first chain cDNA in 20 µl reaction system, and the reverse transcriptase was M-MLV reverse transcriptase purchased from Takara Corporation. Add 1 µl oligo dT, 2 µg RNA and $H_2O$ without RNase up to 13.50 sequentially, denature for 5 min at 70° C. water bath, cool fast for 5 min by ice bath and centrifuge transiently, then add 1 µl 10 mM dNTP, 4 µl 5×RT buffer, 0.5 µl RNase inhibitor and 1 µl reverse transcriptase sequentially. Mix to uniform, react for 60 min at 42° C., and inactivate the reverse transcriptase by 70° C. water bath for 10 min to obtain the first chain cDNA.

Take the first chain cDNA as template to amplify the target gene. The primers used were as follows:

```
BrTCP24-F:
                                        (SEQ ID NO. 3)
5'-GTTCTAGAATGGCAGACGAAGCTCACAACTTTC-3'

BrTCP24-R:
                                        (SEQ ID NO. 4)
5'-GGACTAGTTTAACGATGGCGAGAAATGGAGGAA-3'
```

The reaction system was 25 µl. Add 2.5 µl 10×PCR buffer, 2 µl 2.5 mM dNTP, 2 µl first chain cDNA, 0.5 µl 10 mM forward primer, 0.5 µl 10 mM reverse primer, 0.25 µl 5 U/µl Taq DNA polymerase sequentially, finally add $H_2O$ up to 25 µl.

PCR reaction condition: pre-denature for 3 min at 94° C.; denature for 30 sec at 94° C., anneal for 30 sec at 58° C., extend for 2 min at 72° C., and react for 30 cycles; extend for 10 min finally and hold at 4° C.

After separating the PCR production obtained above by agarose gel electrophoresis, add it into the pUC18 DNA vector. The pUC18 DNA vector was purchased from Takara Corporation. After ligating reaction, transform the ligating production into the *Escherichia coli* DH5α competent cells, check to isolate the positive stain, and obtain the ligated vector.

The ligating reaction system mentioned above was 10 ul. The components included 1 µl pUC18 DNA vector, 2 µl PCR production, 1 µl T4 DNA ligase, and 1 µl 10×reaction buffer. Add $H_2O$ up to 10 ul. The ligating reaction condition mentioned above was reacting for 12-16 hours at 16° C. water bath.

Sequence and confirm the ligated vector. After checking, the nucleotide sequence of the BrTCP24 gene was shown as SEQ ID No. 2, with the full length of 1221 bp, and predicted to encode 406 residues. The AtTCP4 gene of *Arabidopsis thaliana* has a close relationship with BrTCP24 gene in the evolution, wherein the identity of their nucleotide sequences is 77.15% and the identity of amino acid sequences is 77.57%.

Obtaining of the Transgene Plant

Restriction digest the ligated vector mentioned above by XbaI and SpeI endonucleases purchased from Takara Corporation. The operation was as follows:

The reaction system was 50 ul, including 7.5 µl 10×T buffer, 20 µl ligated vector, 2 µl BamHI endonuclease, 2 µl SalI endonuclease, and 18.5 µl $H_2O$; the reaction condition was reacting for 4 hours at 37° C. water bath.

Separate the digested BrTCP24 gene by agarose gel electrophoresis, recycle the gene fragment by Biospin Gel Extraction Kit purchased from Hangzhou Bioer Technology Co., Ltd. The operation was as follows: excise the agarose gel containing the BrTCP24 gene by clean and sharp scalpel, put it in a 1.5 ml centrifuge tube. Add Extraction buffer by 1:3 ratio. Incubate at 50° C. water bath until the gel was completely melted. Transfer the mixture into a Spin column, centrifuge for 1 min at 12000 rpm, discard the liquid in the collection tube. Add 750 ml Wash Buffer into the Spin column, centrifuge for 1 min at 12000 rpm, discard the liquid in the collection tube. Centrifuge again for 1 min at 12000 rpm, transfer the Spin column into a 1.5 ml sterile centrifuge tube. Add 50 μl Elution Buffer into the Spin column, settle for 1 min at room temperature. Centrifuge for 1 min at 12000 rpm, collect the solution containing the BrTCP24 gene. The detailed operation can be referred to the product manual of Biospin Gel Extraction Kit.

Ligate the BrTCP24 gene in the solution into the plant expressing vector pCAMBIA2300-35S-OCS (purchased from Biovector Corporation). The operation was as follows:

The reaction system was 10 ul, including 1 μl pCAMBIA2300-35S-OCS, 5 μl BrTCP24 gene-containing solution, 1 μl 10×T4 ligase buffer and 1 μl T4 ligase. Add $H_2O$ up to 10 ul. The reaction condition was ligating for 12-16 hours at 16° C. water bath.

After reacting mentioned above, the plasmid DNA was obtained. Transform the plasmid DNA into the *Escherichia coli* DH5α competent cells, extract the plasmid for testing, and obtain the constructed plasmid DNA.

Transform the constructed plasmid DNA into *Agrobacterium tumefaciens* LBA4404 (purchased from Biovector Corporation). The operation was as follows:

Electric shock 100 ul *Agrobacterium tumefaciens* LBA4404 cell solution to obtain *Agrobacterium tumefaciens* competent cells, add 3 ul constructed plasmid DNA, cool for 5 min by ice bath, freeze for 1 min by liquid nitrogen, water bath for 5 min at 37° C., then add 1 ml LB medium (1 L LB culture medium contains 5 g yeast extract, 10 g tryptone, 10 g NaCl), and shake for 3 hours at 28° C., 200 rpm. Centrifuge for 1 min at 10000 rpm, discard the supernatant, add 100 ul LB medium to resuspend the cells, spread the resuspended cells on LB plate medium containing 50 mg/L kanamycin and 50 mg/L rifampicin (1 L LB medium plate contains 5 g yeast extract, 10 g tryptone, 10 g NaCl, 15 g agar), culture for 2-3 days at 28° C., and select the transformed Agrobacterium tumefaciens LBA4404.

Transform the transformed *Agrobacterium tumefaciens* LBA4404 into *Arabidopsis thaliana* (*Columbia ecotype*) by floral dip. The operation was as follows:

Inoculate the transformed *Agrobacterium tumefaciens* LBA4404 into 5 ml LB medium, shake overnight at 28° C., 200 rpm, inoculate into 200 ml fresh LB medium by the ratio of 2 wt %, keep on culturing until the $OD_{600}$ reach to 1.0, centrifuge for 5 min at 4500 rpm to collect the bacterial cells, resuspend the bacterial cells in the infected fluid, dip the *Arabidopsis thaliana* inflorescence into the infected fluid for 30 sec, put the flower pot sidelong on the pallet, cover the flower pot with mulching film to avoid light for 24 hours, take away the mulching film on the second day, and make the flower pot stand straight.

The infected fluid included 5 wt % sucrose and 0.03 wt % Tween-20.

Prepare ½ MS screen plate (½ MS medium with 50 mg/L kanamycin and 100 mg/L Carbenicillin). After sterilizing by 70% (v/v) ethanol for 5 min and 2 wt % sodium hypochlorite for 10 min, seed the $T_1$ seeds on the ½ MS screen plate, and each plate was seeded by 100 μg *Arabidopsis thaliana* seeds. After vernalizing for 3 days at 4° C., transfer them into the incubator (16 hours in light/8 hours in dark at 22° C.). After 6 days, select positive plants that were green and growing normally, transfer them onto vermiculite for culturing, harvest the $T_2$ seeds of each plant. Reproduce to gain the $T_3$ generation, identify the $T_3$ generation, and obtain 10 stains of the homozygous transgene plant.

Identifying of the Function of BrTCP24 Gene

Figure 2:
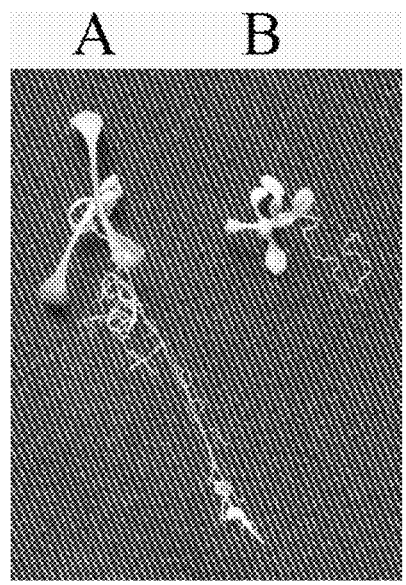
FIG. 2 is the contrast pictures of the wild and transgene *Arabidopsis thaliana* plants growing on ½ MS medium for 20 days. A is the wild type plant, and B is the transgene plant of overexpressing the BrTCP24 gene.

Vernalize the homozygous transgene and wild type *Arabidopsis thaliana* seeds for 3 days in the 4° C. refrigerator. After sterilizing, seed the seeds on the ½ MS medium plate. One part were cultured in the incubator by 16 hours in light/8 hours in dark at 22° C. for 6 days, and the lengths of hypocotyl were measured (the results were shown in Table 1). The other part were cultured in the culturing room (16 hours in light/8 hours in dark at 22° C.), and the weight of the plants was measured and the phenotypes were observed after 20 days (the results were shown in Table 1 and FIG. 2).

After the cotyledon of the seedlings growing on the ½ MS medium plate were expanded fully, transfer the transgene and wild type seedlings onto vermiculite, then culture in the culturing room (16 hours in light/8 hours in dark at 22° C.), observe the phenotypes of the homozygous transgene and wild type plant strains after culturing for 30 days (the results were shown in FIG. 1). It showed that the homozygous transgene plant strain was significantly smaller than the wild type plant stain, indicating that overexpressing the BrTCP24 gene inhibited the growth of plants, and accordingly led to the reduction of the plant organs.

TABLE 1

| variables | wild type plant strain | homozygous transgene plant strain |
|---|---|---|
| *the length of hypocotyl (cm) | 1.61 ± 0.14 | 1.44 ± 0.17 |
| **the weight of the plant (mg) | 11.8 ± 0.26 | 8.5 ± 0.24 |

Note:
*The seedlings have grown in dark for one week;
**The seedlings have grown on ½ MS medium plate for 20 days.

What is claimed is:

1. A BrTCP24 gene for controlling the growth of Chinese cabbage, wherein the BrTCP24 gene has a cDNA having the nucleotide sequence shown as SEQ ID NO: 1.

2. A recombination vector comprises the BrTCP24 cDNA having the nucleotide sequence shown as SEQ ID NO: 1.

3. The recombination vector according to claim 2, wherein the recombination vector is utilized for improving the production of crops.

* * * * *

SEQUENCE LISTING

```
<160> NUMBER OF SEQ ID NOS: 4

<210> SEQ ID NO 1
<211> LENGTH: 1221
<212> TYPE: DNA
<213> ORGANISM: Brassica rapa L. ssp. Pekinensis

<400> SEQUENCE: 1
```

```
atggcagacg aagctcacaa ctttctccac cctccagcac caccaccgcc ttcttcaatg    60
agccaccgcg aggcggcgaa cggcggctgc ggcgagatag tcgaggtgca aggaggtcac   120
attgtccggt cgacgggaag gaaagatcgg cacagcaaag tctgcacggc caagggcca    180 cgtgaccggc gcgtgaggct atcggctcac acggcgattc agttctacga cgttcaggac   240
cgcctcggct tcgaccggcc aagcaaagcc gtcgactggc ttatcaagaa ggctaaagct   300
tccatcgacg agctcgctca gcttccgccg tggaaccccg ccgacgcaat gcgcaacgcc   360
gccgcaaacg cgaaaccgag aagaaccgcc gctaaaactc gaatctctcc gtcgccgccg   420
ccgccgtcgc agcagcaaca gaaccagctt cagttcggtg gattcgacgg agcggcggag   480
catcggggga acgagaacga gtcgagtttt ctcccgccgt cgatggattc ggattctatc   540
gctgacacta taaagtcgtt cttcccggtg gttggctctt cgacggaagc tcctcctccg   600
aaccagctta tacacagcaa ctaccatcat catcacccac cggatttgct ttctcgaact   660
aatagccaca accaagatct ccgtctctcg ctgcactcct tcccggatgg tccaccgtcg   720
cttctccacc accaccactc cgcgtccgcc tccaccgccg agccagttct gttctacggg   780
cagagcaatc cgctagggta tgacacgtcg acgggtggtt gggagcagca gtcaattcag   840
aggctggtgg cttggaacag cggcggagca accgagacag gaaacggagg aggaggagga   900
ggaggagggt ttctctttgc tcctccagct ccttcgacga cgtcgtttca gccagtactt   960
ggccaaagcc cgccttgttc tccgaggggt ccccttcagt ccagttacag tcccatgatc  1020
cgtgcttggt ttgatcctca ccaccaccat cagtccatct ccaccgatga tctcaaccac  1080
catattcctc acccggttca ccaaggtgaa ttctcttccg gtttccgcat accagcacgg  1140
tttcagggcc aagaagagga gcagcacgat ggtttctcca caaaccgtc atctgcttcc  1200 tccatttctc gccatcgtta a                                            1221
```

<210> SEQ ID NO 2
<211> LENGTH: 406
<212> TYPE: PRT
<213> ORGANISM: Brassica rapa L. ssp. Pekinensis

<400> SEQUENCE: 2

```
Met Ala Asp Glu Ala His Asn Phe Leu His Pro Pro Ala Pro Pro Pro
1               5                   10                  15

Pro Ser Ser Met Ser His Arg Glu Ala Ala Asn Gly Gly Cys Gly Glu
                20                  25                  30

Ile Val Glu Val Gln Gly Gly His Ile Val Arg Ser Thr Gly Arg Lys
            35                  40                  45

Asp Arg His Ser Lys Val Cys Thr Ala Lys Gly Pro Arg Asp Arg Arg
        50                  55                  60

Val Arg Leu Ser Ala His Thr Ala Ile Gln Phe Tyr Asp Val Gln Asp
65                  70                  75                  80

Arg Leu Gly Phe Asp Arg Pro Ser Lys Ala Val Asp Trp Leu Ile Lys
                85                  90                  95

Lys Ala Lys Ala Ser Ile Asp Glu Leu Ala Gln Leu Pro Pro Trp Asn
                100                 105                 110

Pro Ala Asp Ala Met Arg Asn Ala Ala Ala Asn Ala Lys Pro Arg Arg
            115                 120                 125

Thr Ala Ala Lys Thr Arg Ile Ser Pro Ser Pro Pro Pro Ser Gln
        130                 135                 140

Gln Gln Gln Asn Gln Leu Gln Phe Gly Gly Phe Asp Gly Ala Ala Glu
```

```
                145                 150                 155                 160
        His Arg Gly Asn Glu Asn Glu Ser Ser Phe Leu Pro Pro Ser Met Asp
                        165                 170                 175

Ser Asp Ser Ile Ala Asp Thr Ile Lys Ser Phe Phe Pro Val Val Gly
                        180                 185                 190

Ser Ser Thr Glu Ala Pro Pro Asn Gln Leu Ile His Ser Asn Tyr
                        195                 200                 205

His His His His Pro Pro Asp Leu Leu Ser Arg Thr Asn Ser His Asn
                        210                 215                 220

Gln Asp Leu Arg Leu Ser Leu His Ser Phe Pro Asp Gly Pro Pro Ser
        225                 230                 235                 240

Leu Leu His His His His Ser Ala Ser Ala Ser Thr Ala Glu Pro Val
                        245                 250                 255

Leu Phe Tyr Gly Gln Ser Asn Pro Leu Gly Tyr Asp Ser Thr Gly
                        260                 265                 270

Gly Trp Glu Gln Gln Ser Ile Gln Arg Leu Val Ala Trp Asn Ser Gly
                        275                 280                 285

Gly Ala Thr Glu Thr Gly Asn Gly Gly Gly Gly Gly Gly Phe
                        290                 295                 300

Leu Phe Ala Pro Pro Ala Pro Ser Thr Thr Ser Phe Gln Pro Val Leu
        305                 310                 315                 320

Gly Gln Ser Pro Pro Cys Ser Pro Arg Gly Pro Leu Gln Ser Ser Tyr
                        325                 330                 335

Ser Pro Met Ile Arg Ala Trp Phe Asp Pro His His His Gln Ser
                        340                 345                 350

Ile Ser Thr Asp Asp Leu Asn His His Ile Pro His Pro Val His Gln
                        355                 360                 365

Gly Glu Phe Ser Ser Gly Phe Arg Ile Pro Ala Arg Phe Gln Gly Gln
                        370                 375                 380

Glu Glu Glu Gln His Asp Gly Phe Ser Asn Lys Pro Ser Ser Ala Ser
        385                 390                 395                 400

Ser Ile Ser Arg His Arg
                        405

<210> SEQ ID NO 3
<211> LENGTH: 33
<212> TYPE: DNA
<213> ORGANISM: Artificial Sequence
<220> FEATURE:
<223> OTHER INFORMATION: Primer sequences for PCR

<400> SEQUENCE: 3
gttctagaat ggcagacgaa gctcacaact ttc                              33

<210> SEQ ID NO 4
<211> LENGTH: 33
<212> TYPE: DNA
<213> ORGANISM: Artificial Sequence
<220> FEATURE:
<223> OTHER INFORMATION: Primer sequences for PCR

<400> SEQUENCE: 4
ggactagttt aacgatggcg agaaatggag gaa                              33
```